(12) United States Patent
Neary et al.

(10) Patent No.: US 8,292,924 B2
(45) Date of Patent: Oct. 23, 2012

(54) ENHANCED PEDICLE ROD CLAMP DEVICE

(75) Inventors: Douglas Wayne Neary, Santa Ana, CA (US); Roger Denis Sung, Colorado Springs, CO (US); Gerald John Alexander, Irvine, CA (US); Susan Kay Bain, Walnut, CA (US); James Monroe Davenport, Kingman, AZ (US)

(73) Assignee: SpineWorks, LLC, Huntington Beach, CA (US)

( * ) Notice: Subject to any disclaimer, the term of this patent is extended or adjusted under 35 U.S.C. 154(b) by 595 days.

(21) Appl. No.: 11/868,357

(22) Filed: Oct. 5, 2007

(65) Prior Publication Data
US 2009/0093848 A1   Apr. 9, 2009

(51) Int. Cl.
*A61B 17/70* (2006.01)
(52) U.S. Cl. ...................................................... 606/250
(58) Field of Classification Search .......... 606/246–279
See application file for complete search history.

(56) References Cited

U.S. PATENT DOCUMENTS

| | | | |
|---|---|---|---|
| 6,238,396 | B1 | 5/2001 | Lombardo |
| 6,352,537 | B1 | 3/2002 | Strnad |
| 6,524,310 | B1 | 2/2003 | Lombardo et al. |
| 2005/0010222 | A1 | 1/2005 | Cordaro |
| 2005/0090821 | A1 | 4/2005 | Berrevoets et al. |
| 2005/0107789 | A1* | 5/2005 | Sweeney .................... 606/61 |
| 2005/0228377 | A1 | 10/2005 | Chao et al. |
| 2006/0064093 | A1 | 3/2006 | Thramann et al. |
| 2006/0116676 | A1 | 6/2006 | Gradel et al. |
| 2006/0149231 | A1 | 7/2006 | Bray |
| 2006/0217718 | A1 | 9/2006 | Chervitz et al. |
| 2006/0259038 | A1 | 11/2006 | Cordaro |

* cited by examiner

*Primary Examiner* — Alvin Stewart
*Assistant Examiner* — Summer Kostelnik
(74) *Attorney, Agent, or Firm* — Knobbe, Martens, Olson & Bear LLP

(57) ABSTRACT

An enhanced pedicle rod clamp device for connecting two or more pedicle rods in spinal surgery is disclosed. The device may include an arm, an upper clamp, and a lower clamp, which are configured for coupling to a pedicle rod. The upper clamp may be coupled to the arm, and the lower clamp may be coupled to the upper clamp. The upper clamp may be rotationally and/or translationally movable with respect to at least one of the arm and the lower clamp. The lower clamp may be rotationally and/or translationally movable with respect to at least one of the arm and the upper clamp.

14 Claims, 4 Drawing Sheets

… (US 8,292,924 B2)

ENHANCED PEDICLE ROD CLAMP DEVICE

BACKGROUND

1. Field

This disclosure relates generally to novel structures of, and approaches to, spinal correction and in particular to connecting and securing two or more pedicle rods. In particular, the present invention relates to cross bars with tightening and closure driven by collet rotation.

2. General Background

Procedures for operating on a spine and devices used therein often employ pedicle rods that are disposed longitudinally along the length of the spine. The pedicle rods may be attached to the spine with pedicle screws anchored into adjoining vertebrae. The pedicle rods, being attached to the pedicle screws or otherwise connected to at least one pedicle of the spine, help maintain a certain position and orientation of each attached vertebra with respect to other vertebrae. Where multiple pedicle rods are employed, each pedicle rod may be stabilized with respect to another pedicle rod by connecting the pedicle rods.

A device that offers medical personnel a larger number of options with regard to the position and orientation of the device with respect to the pedicle rods is a long-felt need not adequately addressed prior to the instant teachings. The instant teachings address and overcome these longstanding needs by providing increased and improved options to medical personnel. Likewise, maintaining spinal stability during and after procedures ameliorates and overcomes artifacts of surgery that are undesirable.

SUMMARY

Briefly stated, an enhanced pedicle rod clamp device is disclosed, offering more and improved options with regard to structures and methods for positioning and orientating the pedicle rod clamp device with respect to two pedicle rods and connecting the pedicle rod clamp device to the two or more pedicle rods.

According to embodiments, a pedicle rod clamp device includes an arm, an upper clamp, and a lower clamp, which are configured for coupling to a pedicle rod. The upper clamp may be coupled to the arm, and the lower clamp may be coupled to the upper clamp. The upper clamp may be rotationally and/or translationally movable with respect to at least one of the arm and the lower clamp. The lower clamp may be rotationally and/or translationally movable with respect to at least one of the arm and the upper clamp.

According to embodiments, a pedicle rod clamp device includes an arm, an upper clamp, and a lower clamp, which are configured for coupling to a pedicle rod. The upper clamp may be coupled to the arm, and the lower clamp may be coupled to the upper clamp. A location of coupling between the upper clamp and the arm and a location of coupling between the lower clamp and the upper clamp may be points along an axis, which may be a line or a curve. The upper clamp may rotate about and/or move translationally along the axis. The lower clamp may rotate about and/or move translationally along the axis comprising a ramp along a leading edge of the lower clamp to persuade placement of a bar.

According to embodiments, a method is also disclosed, which includes the step of providing a pedicle rod clamp device, and emplacement of the same in a patient in need of the same, whereby a collet is closed by a quarter turn and further rotation of a nut causing the pedicle rod to be emplaced and further rotation of the nut closes the clamping space.

DRAWINGS

The above-mentioned features and objects of the present disclosure will become more apparent with reference to the following description taken in conjunction with the accompanying drawings wherein like reference numerals denote like elements and in which.

Figure 3:
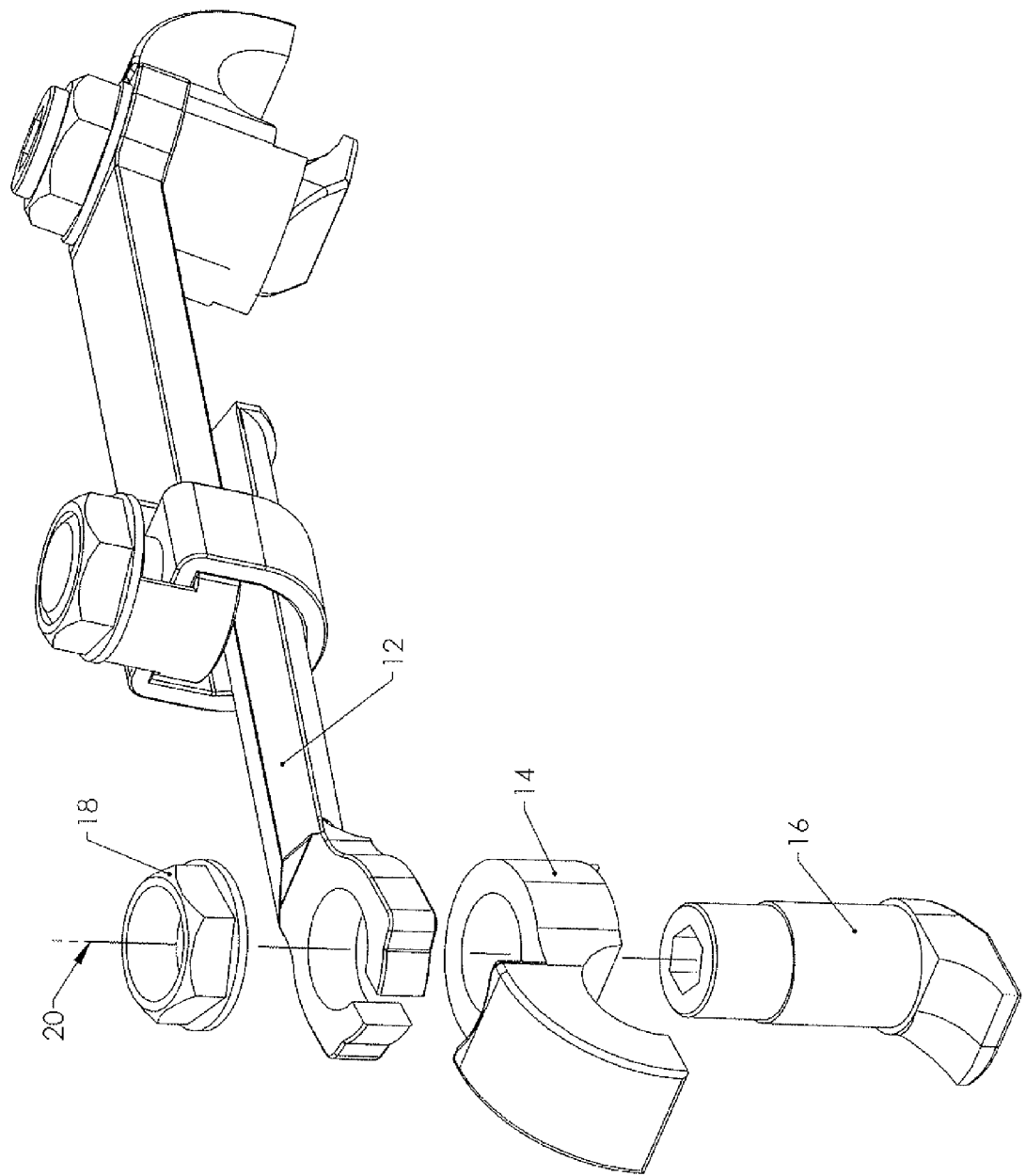
Figure 4:
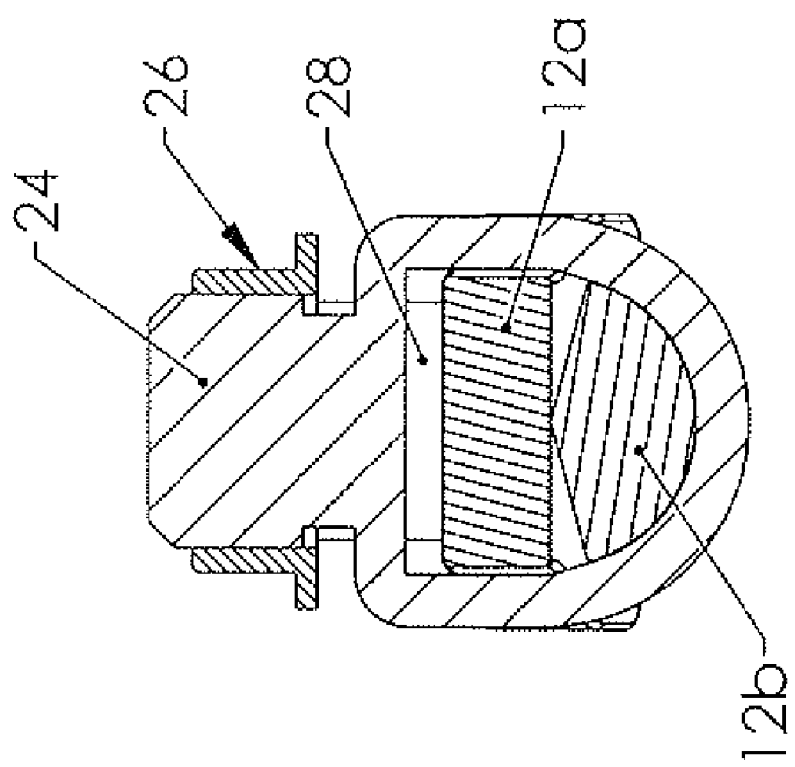

FIG. 3 is a partially exploded view of an embodiment of a pedicle rod clamp device, showing an arm, an upper clamp, a lower clamp, and an outer nut, according to one or more embodiments of the present disclosure; and FIG. 4 is a cross-sectional view of an embodiment of a pedicle rod clamp device, showing a collar, a center nut, an upper arm, and a lower arm, according to one or more embodiments of the present disclosure.

DETAILED DESCRIPTION

Reference will now be made to embodiments, examples of which are illustrated in the accompanying drawings. While the disclosure will be described in conjunction with the preferred embodiments, it will be understood that these embodiments are not intended to limit the scope of the disclosure. On the contrary, the disclosure is intended to cover alternatives, modifications, and equivalents, which may be included within the spirit and scope of the disclosure as defined by the appended claims. As such, the descriptions of the embodiments that follow are for purposes of illustration and not limitation.

Figure 1:
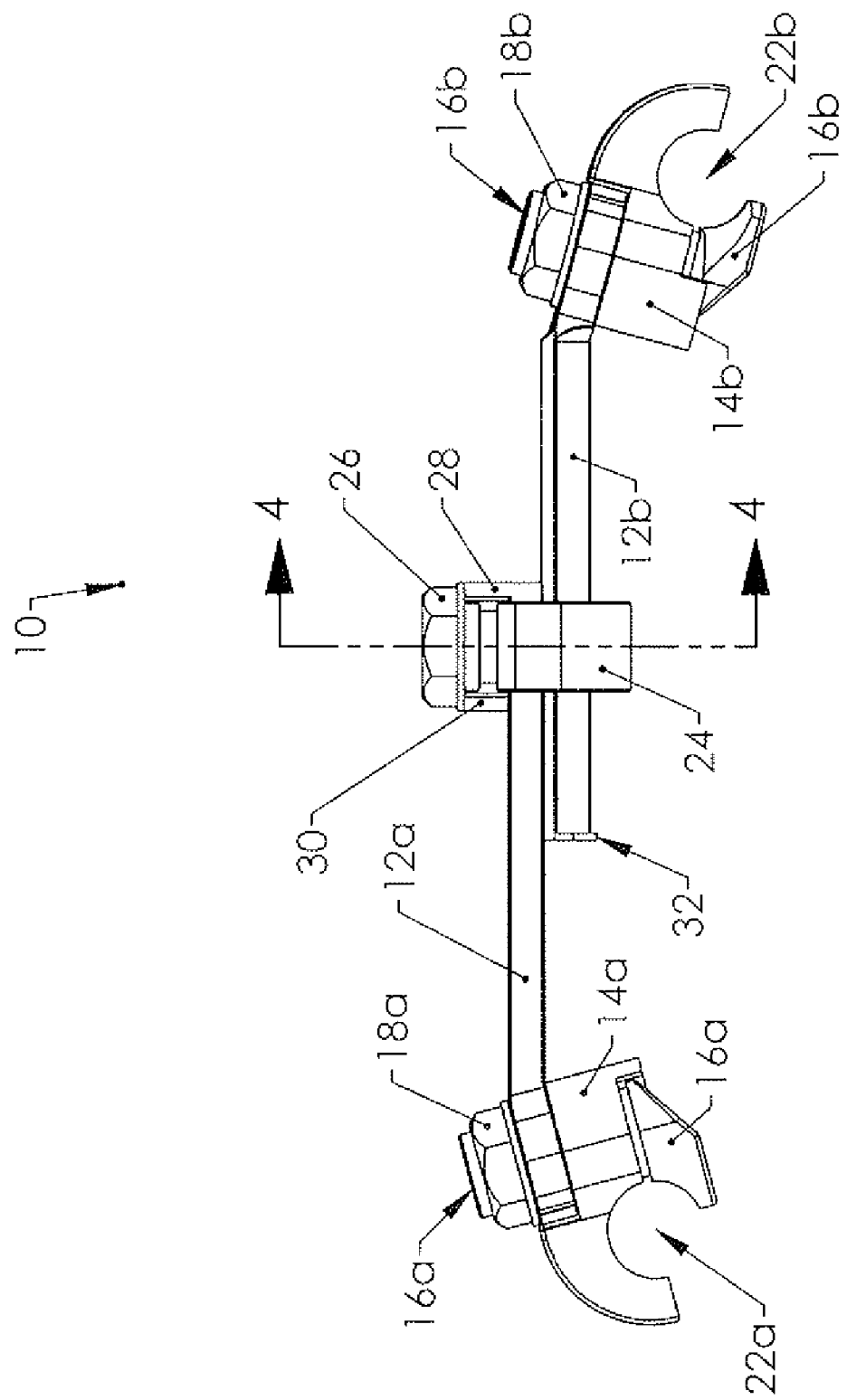
FIG. 1 is a side view of an embodiment of a pedicle rod clamp device, according to one or more embodiments of the present disclosure.

FIG. 1 is a side view of an embodiment of pedicle rod clamp device shown generally at 10, according to one or more embodiments of the present disclosure. Artisans appreciate the instant system as adjustable and configured to optimally support a patient's needs, as determined by qualified care providers.

According to embodiments, pedicle rod clamp device 10 includes upper arm 12a, wherein upper arm 12a may include first upper clamp 14a, first lower clamp 16a, and first outer nut 18a, wherein first upper clamp 14a and first lower clamp 16a form first clamp space 22a. First clamp space 22a may be configured to receive a first pedicle rod (not shown).

According to embodiments, pedicle rod clamp device 10 may also include lower arm 12b, wherein lower arm 12b may include second upper clamp 14b, second lower clamp 16b, and second outer nut 18b, wherein second upper clamp 14b and second lower clamp 16b form second clamp space 22b. Second clamp space 22b may be configured to receive a second pedicle rod (not shown).

According to embodiments, upper arm 12a and lower arm 12b may be fixedly or adjustably coupled. In at least one embodiment, upper arm 12a and lower arm 12b are adjustably coupled such that the distance between first clamp space 22a and second clamp space 22b may be selectively adjusted. For example, the distance between first clamp space 22a and second clamp space 22b may be adjusted to accommodate a first pedicle rod and a second pedicle rod that are separated by a given distance. Such adjustability enables a surgeon, for example, to achieve the manner of structural support needed by a patient whereby tissue insult and injury is mitigated or prevented.

In at least one embodiment, upper arm 12a, first upper clamp 14a, first lower clamp 16a, and first outer nut 18a may each include substantially similar structures as those of lower arm 12b, second upper clamp 14b, second lower clamp 16b, and second outer nut 18b, respectively. For example, first clamp space 22a and second clamp space 22b may be configured to receive a first pedicle rod and a second pedicle rod, wherein the first pedicle rod and the second pedicle rod are each of a substantially similar shape and size. Symmetrical support and load bearing become key features of the present disclosure when optimally emplaced by a skilled surgeon.

Those skilled in the art will recognize that other configurations are possible and within the scope of the present disclosure. For example, each of upper arm 12a and lower arm 12b and their respective components may be configured to couple to any of a pedicle rod, a pedicle screw, a vertebra, or any other object near the pedicle rod clamp device.

With this understanding, reference will now be made to components of embodiments of a pedicle rod clamp device without using the prefix "first" or "second" and without reference to the suffix "a" or "b." It will be understood by those skilled in the art that such references may apply to the components of either, both, or none of upper arm 12a and lower arm 12b. Further, "arm 12" will be understood to refer to either or both of upper arm 12a and lower arm 12b.

Figure 2:
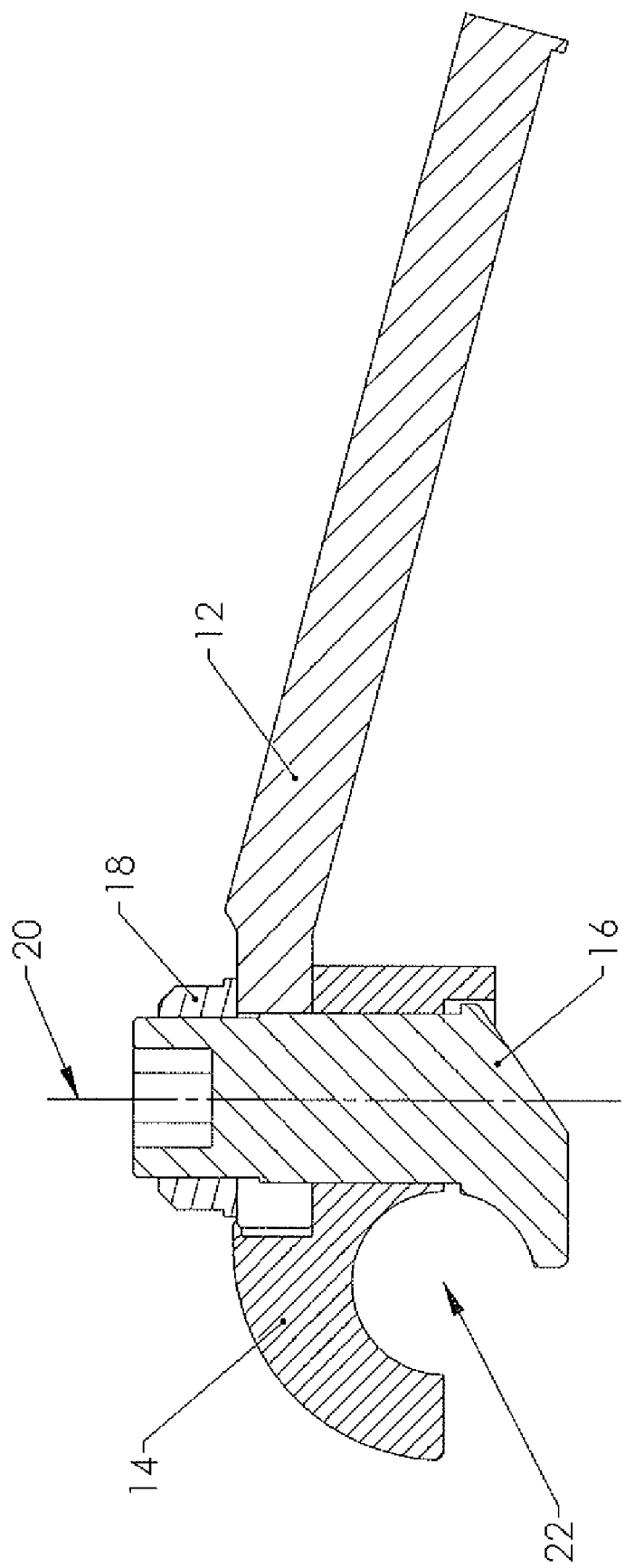
FIG. 2 is a cross-sectional view of an embodiment of a pedicle rod clamp device, showing an arm, an upper clamp, a lower clamp, and an outer nut, according to one or more embodiments of the present disclosure.

FIG. 2 is a cross-sectional view of an embodiment of pedicle rod clamp device shown generally at 10, showing arm 12, upper clamp 14, lower clamp 16, and outer nut 18, according to one or more embodiments of the present disclosure.

According to embodiments, pedicle rod clamp device 10 may include arm 12, upper clamp 14, lower clamp 18, outer nut 20. Upper clamp 16 and lower clamp 18 may determine the shape and size of clamp space 22. For example, the shape and size of clamp space 22 may correspond to the shape and size of the pedicle rod, such that the pedicle rod is securely held within clamp space 22 by upper clamp 14 and lower clamp 18.

FIG. 3 is a partially exploded view of an embodiment of pedicle rod clamp device shown generally at 10, showing arm 12, upper clamp 14, lower clamp 16, and outer nut 18, according to one or more embodiments of the present disclosure.

According to embodiments, lower clamp 16 may be inserted along axis 20 into an opening of upper clamp 14. Lower clamp 16 may also be inserted along axis 20 into an opening of arm 12. Outer nut 18 may secure lower clamp 16. For example, outer nut 18 may be configured to thread onto a portion of lower clamp 16.

According to embodiments, upper clamp 14 may rotate about axis 20 with respect to arm 12 and with respect to lower clamp 16. Lower clamp 16 may rotate about axis 20 with respect to arm 12 and with respect to upper arm 14. Upper clamp 14 may be secured with respect to arm 12 and lower clamp 16. For example, pressure between arm 12 and lower clamp 16 may secure upper clamp 14. Arm 12 may be secured with respect to outer nut 18 and upper clamp 14. For example, pressure between outer nut 18 and upper clamp 14 may secure arm 12. At least one of pressure between arm 12 and lower clamp 16 and between outer nut 18 and upper clamp 14 may be provided by tightening outer nut 18 onto lower clamp 16.

According to embodiments, a surface of arm 12 and a surface of upper clamp 14 may provide friction between arm 12 and upper clamp 14 at an area of contact between arm 12 and upper clamp 14. In at least one embodiment, arm 12 and upper clamp 14 may include at least one tooth configured to allow arm 12 and upper clamp 14 to interlock with respect to each other.

According to embodiments, at least one of a surface of upper clamp 14 and a surface of lower clamp 16 may be configured to provide friction between upper clamp 14 and lower clamp 16 at an area of contact between upper clamp 14 and lower clamp 16. In at least one embodiment, each of upper clamp 14 and lower clamp 16 may include at least one tooth configured to allow upper clamp 14 and lower clamp 16 to interlock with respect to each other.

According to embodiments, the rotation of upper clamp 14 about axis 20 with respect to arm 12 may be limited by the shapes of upper clamp 14 and arm 12. For example, arm 12 may include a protrusion that refuses rotation of upper clamp 14 beyond a certain rotation about axis 20. In at least one embodiment, the rotation of lower clamp 16 about axis 20 with respect to upper clamp 14 may be limited by the respective shapes of lower clamp 16 and upper clamp 14. For example, upper clamp 14 may include a protrusion that refuses rotation of lower clamp 16 beyond a certain rotation about axis 20.

According to embodiments, lower clamp 16 may be configured to move translationally along axis 20 with respect to at least one of upper clamp 14 and arm 12. For example, tightening nut 18 onto lower clamp 16 may cause lower clamp 16 to move translationally toward nut 18; loosening nut 18 from lower clamp 16 may cause lower clamp 16 to move translationally away from nut 18. Those skilled in the art will understand other structures and methods for causing lower clamp 16 to move translationally along axis 20.

According to embodiments, a location of coupling between upper clamp 14 and arm 12 and a location of coupling between lower clamp 16 and upper clamp 14 may be points along an axis 20. In at least one embodiment, axis 20 may be a line, such that lower clamp 16 may move translationally along a linear path formed by axis 20. In at least one embodiment, lower clamp 16 may be a curve, such that lower clamp 16 may move translationally along a curved path formed by axis 20.

FIG. 4 is a cross-sectional view of an embodiment of pedicle rod clamp device shown generally at 10, showing collar 24, center nut 26, upper arm 12a, and lower arm 12b, according to one or more embodiments of the present disclosure. With reference to FIG. 1 and FIG. 4, according to embodiments, upper arm 12a and lower arm 12b may be connected by collar 24 and a center nut 26.

According to embodiments, a portion of upper arm 12a and a portion of lower arm 12b may both be inserted through an opening of collar 24. Arm 12 may include at least one of outer binder 28 and inner binder 30, such that collar 24 does not move translationally along the longitudinal length of arm 12. Center nut 26 may be tightened onto collar 24, such that center nut 26 causes collar 24 to be brought toward center nut 26. In at least one embodiment, tightening center nut 26 onto collar 24 causes upper arm 12a and lower arm 12b to be secured with respect to each other. For example, center nut 26 may come into contact with at least one of outer binder 28 and inner binder 30, such that tightening center nut 26 onto collar 24 causes lower arm 12b to be brought closer to upper arm 12a. While upper arm 12a and lower arm 12b are in contact with each other, friction provided by the contact may prevent upper arm 12a and lower arm 12b from moving with respect to each other. In at least one embodiment, lower arm 12b may include a stopper 32, which prevents lower arm 12b from being removed from the opening of collar 24.

While the apparatus and method have been described in terms of what are presently considered to be the most practical and preferred embodiments, it is to be understood that the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims.

It should also be understood that a variety of changes may be made without departing from the essence of the disclosure. Such changes are also implicitly included in the description. They still fall within the scope of this disclosure. It should be understood that this disclosure is intended to yield a patent covering numerous aspects of the disclosure both independently and as an overall system and in both method and apparatus modes.

Further, each of the various elements of the disclosure and claims may also be achieved in a variety of manners. This disclosure should be understood to encompass each such variation, be it a variation of an embodiment of any apparatus embodiment, a method or process embodiment, or even merely a variation of any element of these.

Particularly, it should be understood that as the disclosure relates to elements of the disclosure, the words for each element may be expressed by equivalent apparatus terms or method terms—even if only the function or result is the same.

Such equivalent, broader, or even more generic terms should be considered to be encompassed in the description of each element or action. Such terms can be substituted where desired to make explicit the implicitly broad coverage to which this disclosure is entitled.

It should be understood that all actions may be expressed as a means for taking that action or as an element which causes that action.

Similarly, each physical element disclosed should be understood to encompass a disclosure of the action which that physical element facilitates.

Any patents, publications, or other references mentioned in this application for patent are hereby incorporated by reference. In addition, as to each term used it should be understood that unless its utilization in this application is inconsistent with such interpretation, common dictionary definitions should be understood as incorporated for each term and all definitions, alternative terms, and synonyms such as contained in at least one of a standard technical dictionary recognized by artisans and the Random House Webster's Unabridged Dictionary, latest edition are hereby incorporated by reference.

Finally, all referenced listed in the Information Disclosure Statement or other information statement filed with the application are hereby appended and hereby incorporated by reference; however, as to each of the above, to the extent that such information or statements incorporated by reference might be considered inconsistent with the patenting of this/these disclosure(s), such statements are expressly not to be considered as made by the applicant(s).

In this regard it should be understood that for practical reasons and so as to avoid adding potentially hundreds of claims, the applicant has presented claims with initial dependencies only.

Support should be understood to exist to the degree required under new matter laws—including but not limited to United States Patent Law 35 U.S.C. §132 or other such laws—to permit the addition of any of the various dependencies or other elements presented under one independent claim or concept as dependencies or elements under any other independent claim or concept.

To the extent that insubstantial substitutes are made, to the extent that the applicant did not in fact draft any claim so as to literally encompass any particular embodiment, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative embodiments.

Further, the use of the transitional phrase "comprising" is used to maintain the "open-end" claims herein, according to traditional claim interpretation. Thus, unless the context requires otherwise, it should be understood that the term "compromise" or variations such as "comprises" or "comprising", are intended to imply the inclusion of a stated element or step or group of elements or steps but not the exclusion of any other element or step or group of elements or steps.

Such terms should be interpreted in their most expansive forms so as to afford the applicant the broadest coverage legally permissible.

The invention claimed is:

1. A pedicle rod clamp device, comprising, in combination: at least one arm, an upper clamp, a lower clamp, and a nut, wherein said upper clamp forms a collet portion configured to partially surround a single pedicle rod, wherein said lower clamp forms a collet portion configured to partially surround said single pedicle rod; wherein said upper clamp is coupled to said arm and said lower clamp is coupled to said upper clamp; wherein said lower clamp is configured to rotate about an axis with respect to said upper clamp when said lower clamp is coupled to said upper clamp; wherein said upper clamp is configured to limit rotation of said lower clamp beyond a certain rotation about said axis; and wherein a threaded upper portion of the lower clamp extends through openings in said arm and said upper clamp, and wherein said threaded upper portion is engaged with the nut.

2. The pedicle rod clamp device of claim 1, wherein said upper clamp is configured to rotate about an axis.

3. The pedicle rod clamp device of claim 1, wherein said lower clamp further comprises a ramp along a leading edge of said lower clamp to persuade placement of the single pedicle rod therein.

4. The pedicle rod clamp device of claim 1, wherein said lower clamp is configured to move translationally along an axis.

5. The pedicle rod clamp device of claim 1, wherein said nut secures said arm and said upper clamp between said nut and said lower clamp.

6. The pedicle rod clamp device of claim 1, wherein said lower clamp is brought closer to said upper clamp by adjusting said nut.

7. The pedicle rod clamp device of claim 1, wherein said upper clamp and said lower clamp form a clamping space, whereby emplacement of the device by a surgeon is made more precise.

8. The pedicle rod clamp device of claim 1, wherein at least ¼ rotation of said lower clamp causes the pedicle rod to be emplaced and further rotation of said nut closes the clamping space.

9. A pedicle rod clamp device, comprising, in combination:

at least one arm, an upper clamp forming a collet portion configured to partially surround a single pedicle rod, and a lower clamp forming a collet portion configured to partially surround the single pedicle rod;

wherein said upper clamp is coupled to said arm;

wherein said lower clamp is coupled to said upper clamp; wherein a threaded upper portion of the lower clamp extends through openings in said arm and said upper clamp, and wherein said threaded upper portion is engaged with a nut;

wherein said upper clamp is movable with respect to said arm; and wherein said lower clamp is movable with respect to said arm independently of said upper clamp and said lower clamp is rotatable with respect to said upper clamp when said lower clamp is coupled to said upper clamp, wherein the upper clamp is configured to limit rotation of said lower clamp beyond a certain rotation; and wherein at least ¼ rotation of said nut causes the pedicle rod to be emplaced by closing a collet around the pedicle rod and wherein further rotation of said nut closes the clamping space.

10. The pedicle rod clamp device of claim 9, wherein said upper clamp is rotationally movable with respect to said arm.

11. The pedicle rod clamp device of claim 9, wherein said lower clamp is rotationally movable with respect to said arm.

12. The pedicle rod clamp device of claim 9, wherein said lower clamp is translationally movable with respect to said upper clamp.

13. A method of cross connecting pedicle rods, the method comprising: closing a collet around a pedicle rod by rotating a nut coupled to a lower clamp to produce at least a ¼ turn of the lower clamp portion and then preventing further rotation of the lower clamp to form a clamping space with the pedicle rod emplaced therein; and closing the clamping space by continuing to rotate the nut to raise the lower clamp to secure the pedicle rod within the clamping space.

14. The method of claim 13, wherein closing the clamping space comprises moving the lower clamp along an axis toward an upper clamp.

* * * * *